United States Patent [19]

Mathew

[11] Patent Number: 4,743,701

[45] Date of Patent: May 10, 1988

[54] PROCESS FOR THE PREPARATION OF ORGANO N-HYDROXYIMIDATES

[75] Inventor: Chempolil T. Mathew, Randolph, N.J.

[73] Assignee: Allied Corporation, Morristownship, N.J.

[21] Appl. No.: 940,148

[22] Filed: Dec. 10, 1986

[51] Int. Cl.$^4$ ............................................. C07C 119/18
[52] U.S. Cl. ............................................. 558/7; 558/6
[58] Field of Search ........................................ 558/6, 7

[56] References Cited

U.S. PATENT DOCUMENTS 2,389,681  11/1943  Mikeska .................................. 558/6
4,339,444   7/1982  D'Silva et al. ......................... 558/6

OTHER PUBLICATIONS

Organic Synthesis—Collective, vol. I, pp. 5-7 (1964).
A. Werner and H. Buss, Chem. Ber. 27, 2193 (1974).
J. Houben and E. Schmidt, Chem Ber. 46 3616 (1913) and Y. Tamura et al., J. Org. Chem 38, 6 1239 (1973).

*Primary Examiner*—John M. Ford
*Assistant Examiner*—Robert C. Whittenbaugh
*Attorney, Agent, or Firm*—Jay P. Friedenson

[57] ABSTRACT

Organo N-hydroxyimidates are prepared by reacting an organonitrile with an organic alcohol and with a hydrogen halide, in the presence of an organic solvent (which may include an excess of the organonitrile reactant), under anhydrous conditions, to form the corresponding organoimidate hydrohalide, and then reacting said organoimidate hydrohalide with a hydroxylamine salt and ammonia gas in the presence of an organic solvent (which can be the excess organonitrile from the first step), under anhydrous conditions, to produce the corresponding organo N-hydroxyimidate.

27 Claims, No Drawings

PROCESS FOR THE PREPARATION OF ORGANO N-HYDROXYIMIDATES

BACKGROUND OF THE INVENTION

1. Field of the Invention

This invention relates to a novel process for preparing organo N-hydroxyimidates. More particularly, this invention is directed to a process for preparing organo N-hydroxyimidates by reacting an organonitrile with an organic alcohol and with a hydrogen halide selected from the group consisting of HCl, HBr and HI, in the presence of an organic solvent, under anhydrous conditions, to form the corresponding organoimidate hydrohalide, and then reacting the resulting organoimidate hydrohalide with a hydroxylamine salt and ammonia gas in the presence of an organic solvent, under anhydrous conditions, to produce the corresponding organo N-hydroxyimidate.

2. Prior Art

Organo N-hydroxyimidates are a known class of compounds and have long been recognized as valuable intermediates in the synthesis of substituted hydroxylamines. Recently, organo N-hydroxyimidates have become valuable intermediates in the production of agricultural and pharmaceutical products.

Classical methods for preparing organo N-hydroxyimidates involve reacting organoimidates with hydroxylamine, the organoimidates being produced from the reaction of organonitriles and alcohols. This approach, however, as reported in U.S. Pat. No. 4,339,444, results in poor yields. Furthermore, this method requires the inconvenient and cumbersome step of handling moisture-sensitive intermediates (e.g., *Organic Synthesis*, Collective, Vol. I, Page 5). Other reported methods involve reaction of corresponding iminoester hydrochloride compounds and hydroxylamine hydrochloride. For example, J. Houben and E. Schmidt, Chem. Ber. 46, 3616 (1913), Y. Tamura et al., J. Org. Chem. 38, 6 1239 (1973) describe the preparation of ethyl N-hydroxyacetimidate by reacting acetiminoethylester hydrochloride and hydroxylamine hydrochloride. The reported yield was 66.3%.

A. Werner and H. Buss, Chem. Ber. 27, 2193 (1894) have reported an attempted reaction of alpha-chlorobenzaldehyde oxime with sodium ethoxide, in which ethyl N-hydroxy benzimidate was identified along with diphenyl urea as reaction products.

Co-pending, commonly assigned application Ser. No. 599,433 of C. T. Mathew et al., filed Apr. 12, 1984, discloses a process for preparing organo N-hydroxyimidates by halogenating the corresponding oxime compound in an organic solvent which does not react with the halogenation agent under the reaction conditions and reacting the resulting 1-halo-substituted oxime compound with the alkali metal or alkaline earth metal salt of an alcohol.

SUMMARY OF THE INVENTION

The present invention provides a process for preparing organo N-hydroxyimidates which comprises reacting an organonitrile of the formula $$R-C\equiv N$$

with an organic alcohol of the formula $$R_1-OH$$

and with a hydrogen halide (HX) wherein X is selected from the group consisting of Cl, Br and I, in the presence of an organic solvent, under anhydrous conditions, at a temperature low enough to maintain the hydrogen halide in solution, to form a solid slurry of an organoimidate hydrohalide of the formula $$\underset{R-C=NH.HX;}{\overset{OR_1}{|}}$$

and reacting said organoimidate hydrohalide with a hydroxylamine salt and ammonia gas, in the presence of an organic solvent, under anhydrous conditions, to produce the corresponding organo N-hydroxyimidate of the formula $$\underset{R-C=NOH}{\overset{OR_1}{|}}$$

wherein R and $R_1$ are, individually, substituted or unsubstituted alkyl, cycloalkyl, aryl or aralkyl wherein permissible substituents are those which are non-reactive to the hydroxylamine salt reactant.

The step of reacting an organoimidate hydrohalide with a hydroxylamine salt and ammonia gas as described above to produce the corresponding organo N-hydroxyimidate is considered to be of itself an inventive advance in this art.

DETAILED DESCRIPTION OF THE INVENTION AND OF THE PREFERRED EMBODIMENTS

The process of the invention consists of two essential steps. In the first step, an organonitrile of the formula $$R-C\equiv N$$

is reacted with an organic alcohol of the formula $$R_1-OH$$

wherein R and $R_1$ are as defined previously, and with a hydrogen halide (HX) wherein X is selected from the group consisting of Cl, Br and I, in the presence of an organic solvent, under anhydrous conditions, at a temperature low enough to maintain the hydrogen halide in solution. A solid slurry of the corresponding organoimidate hydrohalide of the formula $$\underset{R-C=NH.HX}{\overset{OR_1}{|}}$$

is formed.

When R or $R_1$ are alkyl, the preferred number of carbon atoms is from 1-8 and preferably 1-2. Most preferred, R and $R_1$ each contain 1 carbon atom, i.e., each are methyl. Where R or $R_1$ are cycloalkyl, the preferred number of carbon atoms is from 6-12. When R or $R_1$ are aryl, the preferred number of carbon atoms is from 6-16. When R or $R_1$ are aralkyl, the preferred number of carbon atoms is 7-16. When R or $R_1$ are aryl or aralkyl groups, the aromatic rings of such groups may have alkyl substituents. The number of carbon atoms in R and $R_1$ is not critical provided the desired solubility characteristics are achieved.

The permissible substituents in the R or $R_1$ groups, which are non-reactive to the hydroxylamine salt reactant, may be attached to the carbon chain in the R and $R_1$ groups outside the chain as in trifluoromethyl, or may interrupt the R or $R_1$ chain such as in —O— or —S—. Examples of substituents which are not permissible as being reactive to the hydroxylamine salt are nitrile, carbonyl, ester, acid and halogen groups. Persons skilled in the art can readily determine those substituents which are permissible as being non-reactive with hydroxylamine groups and those which are not permissible as being reactive with hydroxylamine groups.

The hydrogen halide reactant is preferably employed in gaseous form. The preferred hydrogen halide reactant is HCl.

Useful inert organic solvents in this reaction step include methylene chloride, toluene, chloroform, acetonitrile, dimethylformamide and toluene. Other suitable inert organic solvents will readily occur to those skilled in the art.

In a preferred embodiment, instead of using an organic solvent in the organonitrile, alcohol, hydrogen halide reaction, an excess of the nitrile reactant is employed which then serves both as a reagent and as a solvent for the reaction. In this way, the imidate hydrochloride is produced in virtually quantitative yield as a slurry from which the solid is separated out readily by filtration. The mother liquor containing the excess of the nitrile can then be reused.

By "anhydrous conditions" is intended to mean substantially free of that amount of water which would interfere with the reaction. In the organonitrile, alcohol and hydrogen halide reaction described above, the anhydrous conditions should not include more than about 1% by weight of water and still preferably not more than about 0.1% by weight of water.

The reaction temperature for the organonitrile, alcohol and hydrogen halide reaction as described above should be low enough to maintain the hydrogen halide in solution. When hydrogen chloride is employed, the preferred temperature range is from about $-10°$ C. to about $+10°$ C. and preferably from about $-5°$ C. to about $+5°$ C.

The stoichiometry of the organonitrile, alcohol, hydrogen halide reaction requires a 1:1:1 molar ratio of reactants. If the organonitrile reactant is to be used as a solvent as described above, a stoichiometric excess of the nitrile relative to the alcohol and hydrogen halide reactants should be used, which should be preferably in the range of about 2-5:1:1 organonitrile/alcohol/hydrogen halide. Extremely large excesses of the organonitrile reactant are not deleterious to the reaction, but an amount in excess of 5:1:1 organonitrile/alcohol/hydrogen halide is not necessary.

An excess of any of the other alcohol or hydrogen halide reactants would not be deleterious but such an excess would not be desirable for reasons of economy.

If a separate organic solvent is employed for this reaction, the solvent should be an inert organic solvent and the preferred proportions of reactants to be employed are equimolar. If a separate solvent is employed in this step, it is necessary to separate same from the solid slurry produced, such as by filtation, if such solvent is incompatible in the second step reaction to produce the organo N-hydroxyimidate. The amount of solvent required, if a separate solvent is used, is that which is sufficient to make an easily handleable slurry of the corresponding imidate hydrochloride.

There is no criticality as to the order of addition of the nitrile and alcohol reactants, but preferably the hydrogen halide is added to a mixture of the nitrile and alcohol with stirring and cooling to the desired temperature in order to control the reaction exotherm. Usually, a solid slurry of the organoimidate hydrohalide begins to form within about 1-5 hours and frequently between about 2-3 hours. The reaction mixture should continue to be stirred and cooled to the desired temperature and usually within 24 hours the reaction is complete.

After completion of the above-described reaction to form the organoimidate hydrohalide, the solid hydrochloride product is separated out readily from the slurry by filtration. If a solvent for the reaction was employed which is incompatible in the second step reaction, the solvent should be separated from the mother liquor. If an excess of the organonitrile reactant was employed as the solvent, the mother liquor containing the nitrile can be reused as reagent and solvent for reaction with alcohol and hydrogen halide as described above.

The separated solid organoimidate hydrohalide is then reacted with a hydroxylamine salt and ammonia gas in a second step in the presence of an organic solvent, under anhydrous conditions, to produce the corresponding desired organo N-hydroxyimidate of the formula

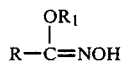

wherein R and $R_1$ are as defined above.

Hydroxylamine salts are a well-known class of reagents. The chloride and sulfate hydroxylamine salts are the better known commercially available salts; however, the phosphate, arsenate and oxalate salts can be prepared by known procedures and are suitable for use in accordance with the invention. Illustrative preparative techniques for these salts are described in *Inorganic Synthesis*, Vol. 3, L. F. Andrieth, McGraw Hill Book Co., (1950), pp. 81-85.

The organic solvent for the second step reaction can be excess organonitrile reactant from the first step or it can be a separate organic solvent in which case such solvent should be an aprotic solvent which is inert in the environment of the second step reaction. Aprotic solvents are well known. Illustrative suitable aprotic solvents for the second step reaction are dimethyl formamide, acetonitrile, methylene chloride, chloroform and toluene. Other suitable aprotic solvents will readily occur to those of ordinary skill in the art.

As indicated, the second step reaction of the organoimidate hydrohalide with the hydroxylamine salt and ammonia gas should be carried out under anhydrous conditions. As in the first step reaction, by "anhydrous conditions" is intended to mean substantially free of that amount of water which would interfere with the reaction. However, the presence of moisture is not as deleterious in the second step as it is in the first step described, but preferably not more than 5% by weight and, still preferably, not more than 1% by weight of water should be present in the reaction mixture in the second step.

The stoichiometry of the second step reaction requires equimolar ratios of the reactants. An excess of any of the reagents will not deleteriously affect the reaction but is unnecessary.

The second step reaction is mildly exothermic and will normally produce temperatures in the range of 20°–40° C. Although not necessary, preferably the exotherm should be controlled so that the reaction temperatures do not exceed about 100° C.

A by-product of the reaction is the inorganic ammonium salt corresponding to the hydroxylamine salt employed. Such inorganic salts can be readily separated from the reaction mixture by filtration. After separation of the salt, the organo N-hydroxyimidate in solution can be isolated by standard distillation or crystallization procedures or used as such for further processing.

In a preferred embodiment of the invention, an excess of the organonitrile reactant is used as solvent in the first step, and the product slurry of organoimidate hydrochloride in the excess of the nitrile is then subjected to reaction with hydroxylamine salt and ammonia as described in the second step above and the ammonium salts are filtered off before isolating the organo N-hydroxyimidate from solution. In this way, the organonitrile functions as solvent in both steps, and a separate organic solvent is not required in either the first step or second step.

The N-hydroxyorganoimidate compounds prepared in accordance with the process of this invention have many and varied uses. For example, such compounds can be reacted with various carbamoyl halide compounds, such as N-methylcarbamoyl chloride, to form the corresponding carbamoyloxime (carbamate) compounds which have pesticidal activity. Such procedures are well known in the Desticidal and organic synthesis arts and will not be described herein.

The following examples illustrate practice of the invention.

EXAMPLE 1

Preparation of Methyl N-Hydroxyacetimidate

A 2-liter, jacketed resin kettle was fitted with an overhead stirrer, a thermometer, a gas sparger and a drying tube. Anhydrous acetonitrile (1000 ml) mixed with absolute methanol (82 grams) was placed in the kettle. The contents were stirred and cooled using a circulating bath and maintained at about 0° C. Anhydrous hydrogen chloride gas (95 grams) was then added from a weighed cylinder through the gas sparger over a period of about 2 hours. Cooling to 0° C. was continued overnight with stirring during which time a white slurry resulted.

Solid hydroxylamine sulfate (215 grams) was added to the white slurry with agitation but without cooling. Anhydrous ammonia gas from a cylinder was then sparged into the slurry over a period of about 5 hours. During this period, a mild exothermic reaction was observed and the temperature reached a maximum of 38° C. Ammonia gas addition was stopped as the temperature began to drop (30° C.), and the slurry was stirred for 2 more hours while the temperature reached ambient.

The resulting white slurry was filtered and a clear, colorless filtrate (916 grams) was collected and analyzed by gas chromotography using an external standard. The yield of methyl N-hydroxyacetimidate in solution was calculated to be 211.5 grams (92.8% yield based on methanol).

The solution was then distilled using a glass wiped-film evaporator under reduced pressure (20 mmHg) at 95° C. and the clear, colorless distillate collected (878 grams) was analyzed by gas chromatography and found to contain 203.6 grams (89.4%) of the acetimidate. The viscous yellowish residue (36 grams) which contained a small amount of the product was discarded.

EXAMPLE 2

Preparation of Ethyl N-Hydroxyacetimidate

A one liter jacketed resin kettle was fitted with an overhead stirrer, a thermometer and a gas sparger. Anhydrous ethanol (113 grams) was mixed with acetonitrile (100 grams) and toluene (400 ml) in the resin kettle. With cooling (to 0° C.) and vigorous stirring, anhydrous HCl gas (95 grams) was sparged into the contents of the resin kettle over a period of about 2 hours. Stirring was continued overnight with cooling, the resulting thick slurry was filtered and a white solid of ethyl acetimidate hydrochloride was collected (283.5 grams). The crude yield was 94.1%.

A portion of this solid (24.7 grams; 0.20 ml) was placed in a 500 ml 3-necked glass fitted with overhead stirring and a thermometer and mixed with dimethyl formamide (200 ml) and solid hydroxylamine sulfate (17.5 grams). With vigorous agitation, anhydrous ammonia gas was slowly introduced at ambient temperature (23° C.), and the temperature rose as high as 45° C. before slowly cooling down. After 1 hour ammonia gas addition was stopped, the mixture was stirred for another hour and then slowly filtered. The resulting white solid cake was discarded and a clear, colorless solution of ethyl N-hydroxyacetimidate in dimethyl formamide was recovered. The product was analyzed by gas chromatography on a 3% FFAP column. Using an external standard, the yield was determined to be 19.3 grams or 3.7%.

EXAMPLE 3

Preparation of Ethyl N-hydroxypropanimidate

A 500 ml, jacketed resin kettle was fitted with an overhead stirrer, a thermometer, a drying tube and a gas bubbler. A charge of propionitrile (60 grams; 1.09 mole), anhydrous ethanol (46 grams; 1.0 mole) and toluene (300 ml) was placed in the reactor. Cooling was started by circulating thermostated coolant through the jacket and the temperature was maintained between −5° and 0° C., while the contents were agitated vigorously. A cylinder of anhydrous HCl gas was set up on a scale and connected to the gas bubbler. With cooling and agitation HCl gas (40 grams; 1.1 mole) was introduced over about 90 minutes. Agitation with cooling was continued overnight (24 hours) and a white slurry resulted. The crystals of ethyl propanimidate hydrochloride (118 grams) were collected through filtration. (Yield 85.8%.)

A part of the solid (45 grams; 0.327 mole) was placed in a 500 ml, 3-neck flask fitted with a thermometer, a gas bubbler and a condenser with a drying tube. A magnetic stirring bar was placed in the flask and the flask with its contents was placed over a stir plate. Dimethyl formamide (165 ml) was added, followed by solid hydroxylamine surfate (29.5 grams; 0.18 mole) and stirrng was started. Anhydrous ammonia gas (6.5 grams; 0.38 mole) was bubbled in from a weighed cylinder slowly over about 4 hours during which time the temperature rose to a maximum of 42° C. and then dropped to 31° C. The white slurry was then cooled in an ice bath and filtered and the clear filtrate (166 grams) was collected.

Gas chromatographic analysis on an FFAP column and GC-mass spectrographic analysis of the solution showed that it contained ethyl N-hydroxypropanimidate (34.3 grams; 89.6% yield).

EXAMPLE 4

Preparation of Ethyl N-hydroxybenzimidate

A resin kettle as described in Example 3 was set up and benzonitrile (51.5 grams; 0.5 mole), absolute ethanol (24.0 grams; 0.52 mole) and toluene (250 ml) were placed in it. With cooling (−5° to 0° C.) and agitation HCl gas (22 grams; 0.60 mole) was introduced and the resulting clear mixture was agitated over two days (44 hours). The resulting white slurry was filtered and ethyl benzimidate hydrochloride was collected as white crystals (85.9 grams; 92.6% yield).

A portion of the solid (21.8 grams; 0.12 mole) was mixed with dimethylformamide (125 ml) and solid hydroxylamine sulfate (10.5 grams; 0.064 mole) in a 500 ml flask and was treated with ammonia gas as described in Example 3. The resulting slurry was then cooled and filtered and the colorless filtrate (113 grams) was collected. On analysis by GC and GC-mass spectroscopy, the filtrate was found to contain virtually pure ethyl N-hydroxybenzimidate (18.9 grams; 95.5% yield) in dimethylformamide solvent.

EXAMPLE 5

Preparation of Methyl N-hydroxyphenylacetimidate

The same equipment as described in Example 3 was used. Benzyl cyanide (38.0 grams; 0.325 mole) was mixed with absolute methanol (10.3 grams; 0.322 mole) and toluene (195 ml). With cooling and agitation HCl gas (16 grams; 0.44 mole) was introduced from a weighed cylinder and the mixture was maintained under the same conditions overnight (26 hours). The resulting white slurry was filtered cold and the solid methyl phenylacetimidate hydrochloride (52.8 grams; 88.4% yield) was collected and a portion of it used directly in the next step.

Methyl phenylacetimidate hydrochloride (30.9 grams; 0.167 mole) was stirred with solid hydroxylamine hydrochloride (12.8 grams; 0.184 mole) in dimethyl formamide (120 ml) while ammonia gas was added slowly without cooling. Ammonia addition (approximately 5 grams) was stopped when the temperature of the mixture peaked at 40° C. and dropped to 29° C. The slurry was then cooled in an ice bath and filtered. The filtrate (131 grams) was analyzed by GC and GC-mass spectroscopy and established to contain methyl N-hydroxyphenylacetimidate (23.4 grams; 84.8% yield).

I claim:
1. A process which comprises:
   (a) reacting an organonitrile of the formula

$$R-C\equiv N$$

with an organic alcohol of the formula $$R_1-OH$$

and with a hydrogen halide (HX) wherein X is selected from the group consisting of Cl, Br and I, in the presence of an organic solvent, under anhydrous conditions, at a temperature low enough to maintain the hydrogen halide in solution to form a solid slurry of an organoimidate hydrohalide of the formula $$\begin{array}{c} OR_1 \\ | \\ R-C=NH\cdot HX \end{array}$$

and
   (b) reacting said organoimidate hydrohalide with a hydroxylamine salt and ammonia gas, in the presence of an organic solvent, under anhydrous conditions, to produce the corresponding organo N-hydroxyimidate of the formula $$\begin{array}{c} OR_1 \\ | \\ R-C=NOH \end{array}$$

wherein R and $R_1$ are, individually, substituted or unsubstituted alkyl, cycloalkyl, aryl or aralkyl, wherein permissible substituents are those which are non-reactive to the hydroxylamine salt reactant.

2. The process of claim 1 in which the solid organoimidate hydrohalide is separated from its mother liquor in said slurry before reaction with the hydroxylamine salt and ammonia gas according to step (b).

3. The process of claim 1 in which the organonitrile reactant is present in sufficient excess of stoichiometric so as to serve as a solvent for the reaction described in step (a).

4. The process of claim 3 in which the solid slurry of organoimidate hydrohalide reaction mixture from step (a) is reacted with the hydroxylamine salt and ammonia gas according to step (b), without first separating out the solid organoimidate hydrohalide.

5. The process of claim 4 in which the resulting ammonium salts from the reaction of step (b) are filtered off before isolating the organo N-hydroxyimidate from the solution in which it is formed.

6. The process of claim 1 in which the X is Cl.

7. The process of claim 3 in which X is Cl.

8. The process of claim 1 in which R and $R_1$ are individually selected from unsubstituted alkyl.

9. The process of claim 8 in which R and $R_1$ are individually selected from the group consisting of methyl and ethyl.

10. The process of claim 3 in which R and $R_1$ are individually selected from the group consisting of methyl and ethyl.

11. The process of claim 7 in which R and $R_1$ are individually selected from the group consisting of methyl and ethyl.

12. The process of claim 1 in which at least one of R and $R_1$ is aryl or aralkyl.

13. The process of claim 12 in which R is aryl.

14. The process of claim 12 in which R is phenyl.

15. The process of claim 12 in which R is benzyl.

16. The process of claim 1 in which R is methyl and $R_1$ is methyl.

17. The process of claim 1 in which R is methyl and $R_1$ is ethyl.

18. The process of claim 1 in which R is benzyl and $R_1$ is ethyl.

19. The process of claim 1 in which R is phenyl and $R_1$ is methyl.

20. The process of claim 1 in which the solid slurry of organoimidate hydrohalide reaction mixture from step (a) is reacted with the hydroxylamine salt and ammonia gas according to step (b), without first separating out the solid organoimidate hydrohalide.

21. The process of claim 20 in which the resulting ammonium salts from the reaction of step (b) are filtered off before isolating the organo N-hydroxyimidate from the solution in which it is formed.

22. A process which comprises reacting an organoimidate hydrohalide of the formula

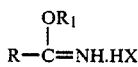

wherein X is selected from the group consisting of Cl, Br and I, with a hydroxylamine salt and ammonia gas in the presence of an organic solvent, under anhydrous conditions, to produce the corresponding organo N-hydroxyimidate of the formula

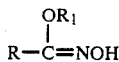

wherein R and $R_1$ are, individually, substituted or unsubstituted alkyl, cycloalkyl, aryl or aralkyl wherein permissible substituents are those which are non-reactive to the hydroxylamine salt reactant.

23. The process of claim 22 in which X is Cl.

24. The process of claim 22 in which the organic solvent is an organonitrile.

25. The process of claim 22 in which the organic solvent is an inert aprotic solvent.

26. The process of claim 22 in which R and $R_1$ are individually selected from the group consisting of methyl and ethyl.

27. The process of claim 22 in which R is an aryl or aralkyl group.

* * * * *